United States Patent
Shaw et al.

(10) Patent No.: US 9,295,790 B2
(45) Date of Patent: Mar. 29, 2016

(54) SYRINGE WITH RECESSED NOSE AND PROTECTIVE GUARD FOR USE WITH FRONTAL ATTACHMENTS

(75) Inventors: Thomas J. Shaw, Frisco, TX (US); Ni Zhu, Plano, TX (US); Gary Wood, Frisco, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 1097 days.

(21) Appl. No.: 12/030,637

(22) Filed: Feb. 13, 2008

(65) Prior Publication Data
US 2008/0132851 A1   Jun. 5, 2008

Related U.S. Application Data

(63) Continuation-in-part of application No. 11/743,706, filed on May 3, 2007, now abandoned.

(60) Provisional application No. 60/798,433, filed on May 5, 2006.

(51) Int. Cl.
| | |
|---|---|
| *A61M 5/34* | (2006.01) |
| *A61M 39/26* | (2006.01) |
| *A61M 39/10* | (2006.01) |
| *A61M 5/31* | (2006.01) |

(52) U.S. Cl.
CPC ............... *A61M 5/347* (2013.01); *A61M 39/26* (2013.01); *A61M 39/10* (2013.01); *A61M 2005/3104* (2013.01); *A61M 2005/3118* (2013.01); *A61M 2005/341* (2013.01); *A61M 2039/267* (2013.01)

(58) Field of Classification Search
CPC ............... A61M 2005/3118; A61M 2005/341; A61M 5/347
USPC ......... 604/181, 187, 188, 199, 218, 240, 241, 604/242, 243, 246, 533, 534, 535, 905; 128/912, 917, 919
See application file for complete search history.

(56) References Cited

U.S. PATENT DOCUMENTS

| | | | |
|---|---|---|---|
| 1,668,315 A | 5/1928 | Hein George N | |
| 2,158,593 A * | 5/1939 | Scrimgeour | 604/242 |
| 4,123,091 A * | 10/1978 | Cosentino et al. | 285/39 |
| 4,326,569 A * | 4/1982 | Vaillancourt | 141/383 |
| 4,490,142 A | 12/1984 | Silvern | |
| 4,624,393 A * | 11/1986 | Lopez | A61J 1/06 222/83.5 |
| 4,718,463 A | 1/1988 | Jurgens, Jr. et al. | |
| 4,743,233 A * | 5/1988 | Schneider | 604/192 |
| 4,747,835 A | 5/1988 | Sandhaus | |
| 4,838,869 A | 6/1989 | Allard | |

(Continued)

FOREIGN PATENT DOCUMENTS

| | | | |
|---|---|---|---|
| CN | 2628071 Y | * | 7/2004 |
| EA | 200600319 A1 | | 6/2007 |

(Continued)

*Primary Examiner* — Kevin C Sirmons
*Assistant Examiner* — Shefali Patel
(74) *Attorney, Agent, or Firm* — Ross Barnes LLP; Monty L. Ross; Robin L. Barnes (57) ABSTRACT

A medical device connectable to a frontal attachment, the medical device having a forwardly projecting fluid outlet member and a forwardly projecting protective guard extending beyond the outlet member to protect the outlet member from pathogenic contamination by contact prior to connection to the frontal attachment.

14 Claims, 8 Drawing Sheets

(56) References Cited

U.S. PATENT DOCUMENTS

| | | | |
|---|---|---|---|
| 5,205,833 | A | 4/1993 | Harsh et al. |
| 5,322,515 | A | 6/1994 | Karas et al. |
| 5,419,775 | A | 5/1995 | Haffner et al. |
| 5,531,699 | A | 7/1996 | Tomba et al. |
| 5,573,516 | A | 11/1996 | Tyner |
| 5,616,136 | A | 4/1997 | Shillington et al. |
| 5,694,686 | A | 12/1997 | Lopez |
| 5,702,367 | A | 12/1997 | Cover et al. |
| 5,807,343 | A | 9/1998 | Tucker et al. |
| 5,827,244 | A * | 10/1998 | Boettger ............... A61M 39/10 604/533 |
| 5,902,271 | A | 5/1999 | Jentzen |
| 5,919,169 | A | 7/1999 | Grams et al. |
| 5,980,495 | A | 11/1999 | Heinz et al. |
| 6,068,614 | A | 5/2000 | Kimber et al. |
| 6,090,077 | A | 7/2000 | Shaw |
| 6,126,640 | A * | 10/2000 | Tucker et al. ................. 604/187 |
| 6,217,550 | B1 * | 4/2001 | Capes ........................... 604/110 |
| 6,382,204 | B1 | 5/2002 | Jansen et al. |
| 6,517,516 | B1 | 2/2003 | Caizza |
| 6,544,233 | B1 | 4/2003 | Fukui et al. |
| 6,740,060 | B2 | 5/2004 | Tanaka et al. |
| 6,758,833 | B2 | 7/2004 | Lopez |
| 7,014,622 | B1 | 3/2006 | Pressly, Sr. et al. |
| 2002/0004648 | A1 | 1/2002 | Larsen et al. |
| 2003/0149403 | A1 | 8/2003 | Barker et al. |
| 2003/0199847 | A1 * | 10/2003 | Akerlund et al. ............. 604/411 |
| 2004/0087906 | A1 | 5/2004 | Henderson et al. |
| 2007/0260189 | A1 | 11/2007 | Shaw et al. |
| 2007/0293824 | A1 | 12/2007 | Brand et al. |

FOREIGN PATENT DOCUMENTS

| | | |
|---|---|---|
| JP | 6181985 | 7/1994 |
| JP | 20021722166 | 6/2002 |
| SU | 23565 | 10/1931 |
| WO | WO 93/11828 | 6/1993 |
| WO | WO 94/13345 | 6/1994 |
| WO | WO2005/065767 | 7/2005 |
| WO | WO2006/099441 | 9/2006 |

* cited by examiner

SYRINGE WITH RECESSED NOSE AND PROTECTIVE GUARD FOR USE WITH FRONTAL ATTACHMENTS

RELATED APPLICATION

This application is a continuation-in-part of and claims the benefit of priority from U.S. patent application Ser. No. 11/743,706 filed May 3, 2007, and from U.S. provisional patent application No. 60/798,433 filed May 5, 2006.

BACKGROUND OF THE INVENTION

1. Field of the Invention

This invention relates to a medical device, in a preferred embodiment a syringe, either traditional or pre-filled, having a recessed nose and a forwardly projecting, protective guard that cooperate to reduce the likelihood of contamination from accidental or inadvertent contact. The syringe of the invention is intended for use in combination with a frontal attachment such as, for example, a sealing cap, a safety cap, a needle assembly, a luer connector, a CLAVE® connector for introducing liquid into a closed IV system, or another vascular access connector or other proprietary or commercially available frontal attachments. The invention also relates to a structure that protects the nose of a syringe from contamination by contact while simultaneously providing full engagement between cooperating surfaces of a connector provided for frontal attachment to the syringe and reducing the likelihood of disengagement during use. The invention also relates to a method for protecting the tip of a luer connector from contamination without reducing the engagement surface area between the luer of a frontal attachment and the nose of a syringe, thereby reducing the likelihood of fluid leakage at the connection between the frontal attachment and the syringe.

2. Description of Related Art

Catheter-associated bloodstream infections reported from hospitals across the United States have increased since the introduction of needleless devices. According to the U.S. Center for Disease Control, an estimated 250,000 catheter-related bloodstream infections occur in U.S. hospitals each year. Catheter-related infections can cost the U.S. healthcare system up to $25,000 per episode or more. As many as 28,000 patients die each year in the U.S. because of catheter-related bloodstream infections.

Syringes that utilize frontal attachments such as sealing caps or various types of connectors rather than fixed needles or preset retractable needles for storing, administering or withdrawing medications or fluids are known in the prior art. Syringes made for use with frontal attachments include pre-filled syringes and standard syringes that are shipped without an affixed needle. Such conventional syringes frequently comprise an annular skirt, collar or other opening at or near the front of the syringe barrel in combination with a smaller-diameter nose portion that extends forwardly beyond the annular skirt or collar at the front end of the barrel. Some syringes with attachable needles have a safety mechanism that encircles a portion of the nose but does not protect the tip from contact prior to use. Other syringes have a protective sheath that the user can slide forward over a needle following use.

Some syringes having a radially spaced-apart annular skirt or collar surrounding a part of the nose also comprise structural elements useful for attaching a needle assembly or other connector to the syringe. With pre-filled syringes, the forwardly extending end of the nose portion is generally either sealed with a membrane to prevent loss of the pre-filled medicament prior to use, or else the syringe is provided with a removable sealing cap that is removed before the needle assembly or connector is attached to the syringe barrel. Once the sealing membrane has been punctured or the sealing cap has been removed, the syringe plunger is depressed and pre-filled liquid flows through the attachment.

Two commercially available types of frontal attachments or connectors are, for example, a CLAVE® connector and a luer connector. The CLAVE brand connector is marketed by ICU Medical and disclosed in U.S. Pat. No. 5,694,686. The CLAVE® connector has a rearwardly facing needle or other sharp object that punctures a sealing membrane in the forwardly extending nose of a prefilled syringe as the connector is threaded into engagement with a collar on the syringe barrel. Following attachment of the CLAVE® connector to both the syringe barrel and to an IV injection port, the syringe plunger is depressed and the pre-filled liquid flows out of the syringe through the shaft of the puncturing needle, through the body of the connector and into the closed intravenous ("IV") injection system. Other syringes that do not have a permanently affixed needle frequently use a frontal attachment comprising a needle and a luer fitting that is attachable to a cooperatively configured syringe barrel. A luer needle attachment typically has either a flange or external threads that are alignable and engageable with cooperating structural elements disposed inside the annular skirt portion near the front of a syringe barrel.

Although both types of conventional syringes as discussed above commonly have an annular skirt near the front of the syringe barrel, such conventional syringes are not known to embody a structure that effectively protects or guards the forwardly extending nose portion of the syringe barrel from contamination by direct contact. Such contact can result in the accidental injection of harmful bacteria or other pathogens into a patient's body, thereby contributing to the spread of disease and potentially fatal bacterial or viral infections within supposedly sterile healthcare environments. This risk is believed to be reduced significantly by the invention disclosed and claimed herein.

SUMMARY OF THE INVENTION

Medical devices intended for use with frontal attachments, such as sealing caps, needle assemblies or needleless connectors, are disclosed herein that substantially reduce the likelihood of accidental pathogenic contamination due to inadvertent contact with the nose of the device. The preferred devices of the present invention are syringes designed so that the nose of each syringe is recessed inside a protective guard that projects forwardly beyond the tip of the nose. The protective guard is desirably either disposed in a fixed axial position relative to the syringe body, or is forwardly biased relative to the syringe body so that it remains in its protective position extending forwardly of the tip of the nose until the biasing force is overpressured to uncover the tip of the nose during connection of a frontal attachment to the syringe. The preferred devices are desirably compatible with commonly available frontal attachments including, for example, sealing caps, safety caps, hypodermic needle assemblies, luer connectors, CLAVE® connectors or other vascular access connectors, or other proprietary or commercially available frontal attachments, vial access devices, and luer-activated catheter hubs. Hypodermic needle assemblies can further comprise integrated needle safety components such as, for example, slidable sheaths, pivotable covers and other devices that are designed to protect health care workers from exposure to contaminated sharps. The preferred devices do not transfer contaminants to luer-activated valves or patients. Unlike some devices disclosed in the prior art, the medical devices disclosed herein comprise a structure that distributes and transfers forces generated during threaded engagement of a vascular access connector to a syringe barrel.

The protective guard of the invention can be made as a unitary part of the body of a medical device, or can be separately made and attached in fixed relation to the device, or can be made so that it is moveable relative to the body of the device. Any frontal attachment to be used with the device is preferably directly attachable to a mounting structure that is disposed in fixed relation to a syringe body. The protective guard of the subject syringes can optionally comprise additional elements that facilitate connection of a sealing cap, needle assembly, needleless connector or other frontal attachment to another portion of the syringe body.

According to one preferred embodiment of the invention, a syringe is provided that comprises a forwardly extending nose, a protective guard projecting forwardly beyond the tip of the nose, and a mounting structure useful for selectively attaching a frontal attachment to the syringe. According to one particularly preferred embodiment of the invention, the syringe barrel, nose, protective guard and mounting structure are made as a unitary structure. Alternatively, the mounting structure can be manufactured as part of a separate but permanently attachable protective guard or as a unitary part of the syringe body. If made separately from the syringe body, the protective guard can be made so that it is releasably or unreleasably attachable to the syringe body during assembly of the syringe prior to sterilization.

According to other preferred embodiments of the invention, the syringe and/or the protective guard are made of plastic, glass, or another similarly effective polymeric or non-polymeric material. The protective guard can be substantially rigid or flexible as desired, depending upon the material, the physical configuration, and the method of construction. The protective guard is desirably mounted in fixed axial relation to the syringe body, or alternatively, is mountable to the syringe body in such manner that it can be selectively retracted to uncover the tip of the nose that is otherwise protected by the guard.

According to another embodiment of the invention, the forwardly projecting guard is a forwardly projecting, substantially cylindrical outer wall, and further comprises means by which the frontal attachments are connected to the syringe. Because the guard projects forwardly beyond the tip of the nose, the nose is protected from accidental contamination due to inadvertent, incidental contact with a clinician or with objects or surfaces proximal to the syringe prior to affixing the frontal attachment.

According to another embodiment of the invention, a pre-filled syringe comprises an elongated hollow syringe body made from either glass or plastic. The syringe body has an open nose with a reduced cross-sectional area in the front and an open back end. Disposed in the hollow body is a plunger comprising a plunger seal in sliding sealed contact with the interior wall of the body. The one-piece plunger seals the back end of the syringe body and has a surface for applying thumb force during injections. The nose of the syringe body is preferably sealed with a removable sealing cap. Because the fluid chamber of the syringe is sealed on both ends, the syringe can be pre-filled with liquid and stored until it is used.

According to another embodiment of the invention, a pre-filled syringe is disclosed that comprises the forwardly projecting guard of the invention and is suitable for use with a CLAVE® connector. The pre-filled syringe of this invention is designed such that the nose tip of the syringe is disposed inwardly of an outer wall of the protective guard that extends beyond the tip of the nose. The recessed nose is protected from contamination due to accidental contact with contaminants prior to attachment of the CLAVE® connector, thereby helping prevent the spread of disease.

According to another preferred embodiment, the nose of the disclosed pre-filled syringe is protected by and recessed behind a forwardly projecting guard that is part of the syringe body. This forwardly projecting structure prevents contaminating physical contact between the user and the recessed nose after the sealing cap has been removed. The forwardly projecting structure does not completely enclose and cover the recessed nose, but instead protrudes past the tip to prevent inadvertent contaminating contact with the nose. The projecting structure, whether or not it solidly encircles the nose of the syringe, should block, interfere with or otherwise prevent human physical contact with the nose during normal use to protect the nose from contamination.

According to another embodiment of the invention, a forwardly projecting guard is incorporated onto a standard, non-pre-filled syringe configured so that a needle can be attached using a conventional luer connector. Luer connectors are well known in the art. The present invention protects the nose of a syringe from contamination by contact while simultaneously providing full engagement between cooperating surfaces of a luer connector securing a frontal attachment to the syringe and reducing the likelihood of accidental disengagement during use.

According to another embodiment of the invention, a method is provided for protecting the tip of a luer connector from contamination without reducing the engagement surface area between the luer of a frontal attachment and the nose of a syringe. This reduces the likelihood of fluid leakage at the connection between the frontal attachment and the syringe. According to one preferred embodiment of the invention, the subject method comprises providing a syringe having a forwardly projecting guard protecting the nose of a syringe and having an engagement surface that facilitates substantially full engagement of the syringe with a cooperating engagement surface of a frontal attachment and that distributes and transfers to the syringe barrel the forces generated during engagement of the frontal attachment.

According to another preferred embodiment of the invention, the forwardly projecting guard is unitarily molded or otherwise permanently affixed or attached, such as by sonically welding, gluing, or the like, to the syringe body during manufacture.

According to another embodiment of the invention, a medical device for use with frontal attachments is provided that comprises a nose, a mounting structure in fixed relation to the nose that surrounds the nose and is internally threaded but does not extend forwardly of the nose, and a protective guard that is normally biased to a position in which it extends beyond the tip of the nose, but is moveable to a position in which the tip of the nose is exposed during connection of a frontal attachment. Prior to use, when the protective guard is biased in its forwardly extending position, the nose is recessed and protected from contamination.

According to another embodiment of the invention, a structure is disclosed that will simultaneously protect the nose of a medical device intended for use with a frontal attachment from becoming contaminated prior to use and will also reduce the likelihood of the frontal attachment becoming disengaged from the medical device during use.

According to another embodiment of the invention, a method is disclosed for protecting the tip of a luer connector that is part of a medical device from contamination without diminishing accessibility to the length of the connector by providing a protective guard that projects forwardly beyond the nose to which a luer connector is attachable. The forwardly extending guard preferably does not compromise the integrity of a standard luer interface with a frontal attachment.

BRIEF DESCRIPTION OF THE DRAWINGS

The apparatus of the invention is further described and explained in relation to the following figures of the drawings wherein.

DESCRIPTION OF THE PREFERRED EMBODIMENTS

Figure 1:
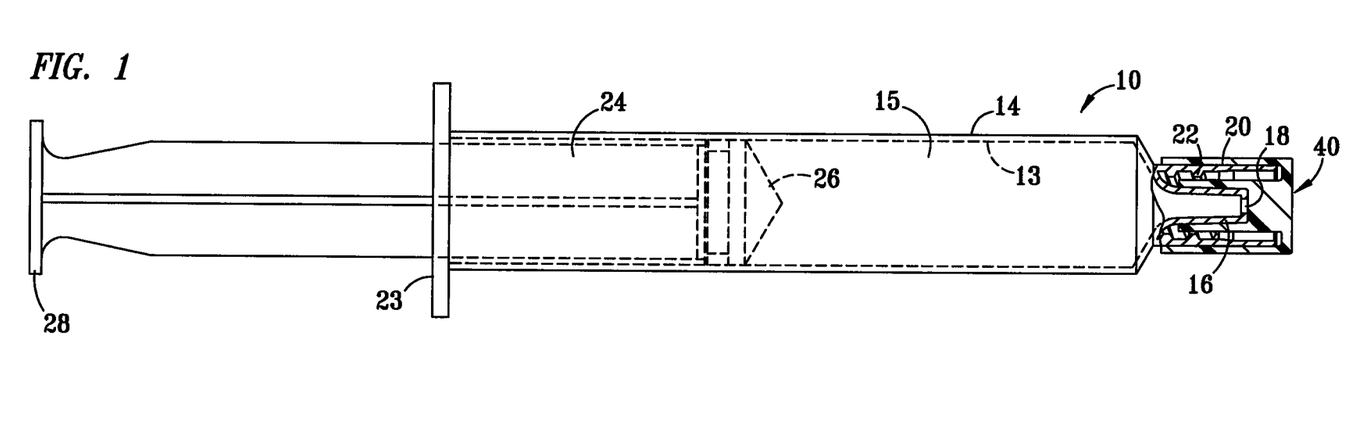
FIG. 1 is a side elevation view, partially in section, of one embodiment of a syringe of the invention having a sealing cap, as can be used with a pre-filled syringe, shown in place over a guard projecting forwardly of the nose of the syringe.
Figure 2:
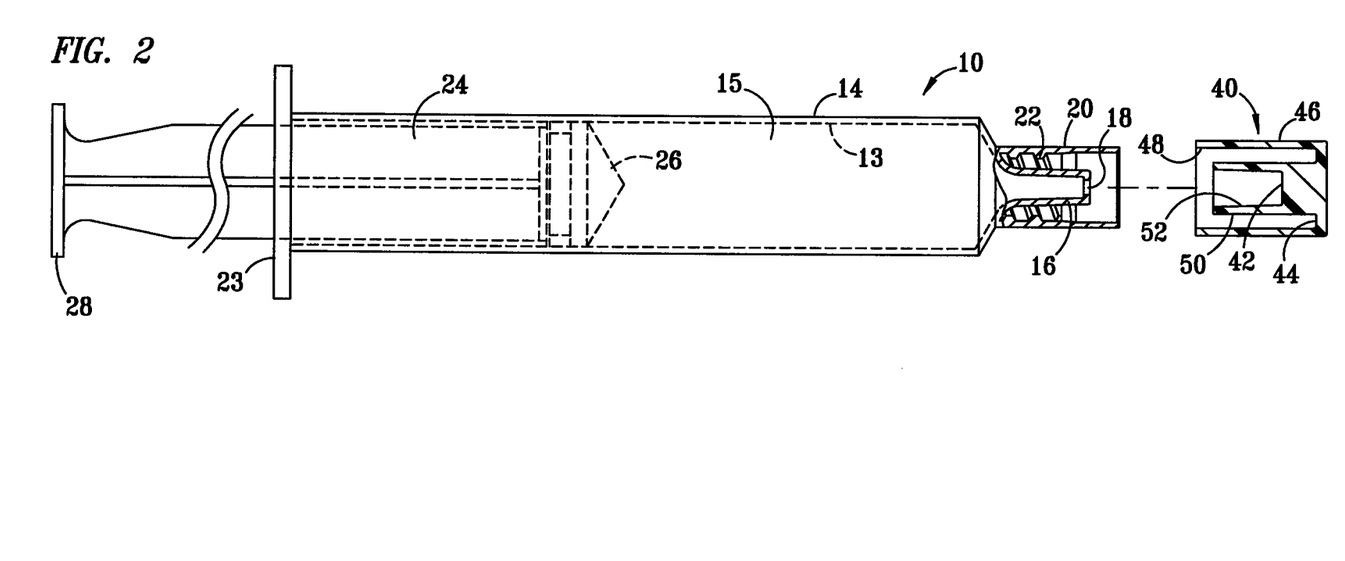
FIG. 2 is an exploded side elevation view, partially in section, of the syringe of FIG. 1, with the sealing cap removed.

Referring to FIGS. 1 and 2, pre-filled syringe 10 has a body preferably comprising tubular barrel 14, plunger 24, and a front end portion or nose 16, which has a reduced cross-sectional area relative to the barrel 14, and an open back end portion 23. The body of syringe 10 is preferably molded from a substantially transparent polymeric resin such as polypropylene, but other materials such as other polymeric resins or glass are also acceptable for use in the invention subject to other parameters referred to in this disclosure.

Disposed in the back end portion 23 of the barrel 14 is a plunger 24 having a rearwardly projecting handle and a plunger seal 26, which may or may not be a separate piece, in sliding sealed contact with interior wall 13 of barrel 14. Plunger 24 seals back end portion 23 of syringe barrel 14 and has an end cap 28 for applying thumb force to depress plunger 24 and discharge medication from syringe 10 during use. Nose 16 of syringe 10 has an axial bore with a forwardly facing opening 18, and nose 16 is desirably covered prior to use with removable sealing cap 40. When both open back end portion 23 and nose 16 of the syringe barrel 14 are sealed prior to use, syringe 10 can be pre-filled with liquid in variable fluid chamber 15. Once the syringe 10 is filled, vacuum pressure along with friction between plunger 24 and interior wall 13 will keep plunger 24 in place.

As shown in this embodiment, forwardly projecting, protective guard 20 is unitarily molded as part of the body of pre-filled syringe 10, and extends forwardly past nose 16. Sealing cap 40 is preferably a two-walled structure that slides into engagement over both projecting guard 20 and nose 16. Inner edge 48 of outer wall 46 of sealing cap 40 slidably engages the outside of projecting guard 20. Inner edge 52 of inner wall 50 of sealing cap 40 slidably engages the outside of nose 16. As sealing cap 40 slides into engagement on pre-filled syringe 10, projecting guard 20 seats against stop 44 and nose 16 seats against stop 42. When the tip of nose 16 seats against stop 42, nose opening 18 is sealed. Alternatively, sealing cap 40 can have an elastomeric plug or cover placed in or around nose opening 18, in which case outer wall 46 is unnecessary in order to achieve a fluid-tight seal. At the time of use, sealing cap 40 is removed from pre-filled syringe 10 while the syringe is held with the nose in an upright position, thus unsealing nose opening 18 and also avoiding spillage prior to connecting a frontal attachment device.

Figure 3:
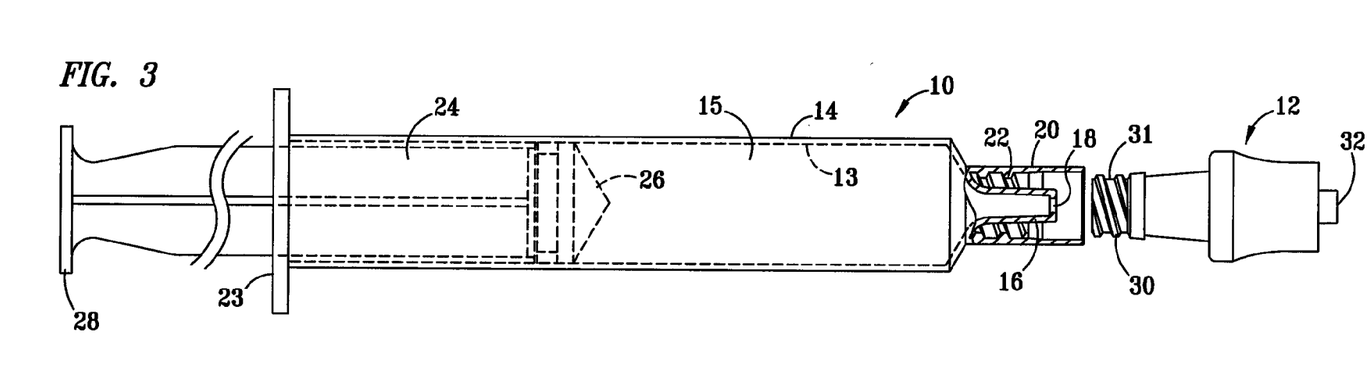
FIG. 3 is a side elevation view, partially in section, of the syringe of FIG. 2 that is coaxially aligned with a CLAVE® connector prior to attachment of the CLAVE® connector to the syringe.
Figure 4:
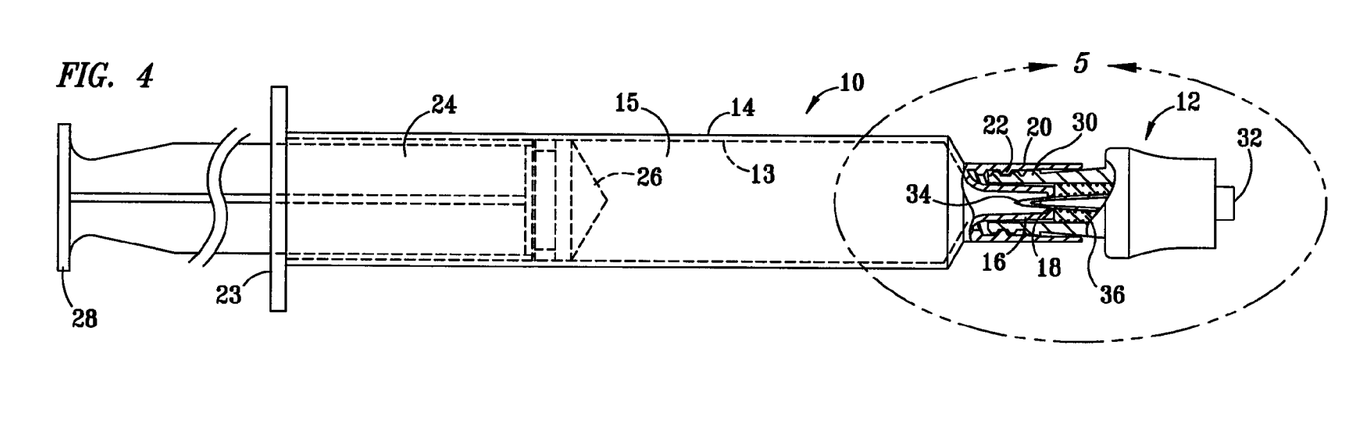
FIG. 4 is a side elevation view, partially in section, of the syringe and CLAVE® connector of FIG. 3 after the CLAVE® connector has been attached to the front portion of the syringe.

Referring to FIGS. 3 and 4, in a preferred embodiment inner wall 22 of forwardly projecting guard 20 is threaded to accept the cooperative threads 30 on a CLAVE® connector 12 once the sealing cap is removed. The CLAVE® connector is preferably attached to the syringe while the nose is being held in an elevated position relative to the remainder of the variable fluid chamber inside the syringe. The forwardly projecting guard 20 is desirably sized and configured so that it extends beyond nose 16 and so that the inner diameter is slightly larger than the outer diameter of CLAVE® connector 12.

A standard CLAVE® connector 12 has a forwardly facing open end 32, which is connectable to a closed IV system. The CLAVE® connector 12 has a back section 31, with external threads 30. External threads 30 allow CLAVE® connector 12 to be threaded into forwardly projecting guard 20 of pre-filled syringe 10. Referring specifically to FIG. 4, CLAVE® connector 12 has a rearwardly facing needle 34 that is encircled by back section 31. Rearwardly facing needle 34 is in fluid communication with open front end 32. Elastomeric support structure 36 restrains lateral movement of needle 34.

Figure 5:
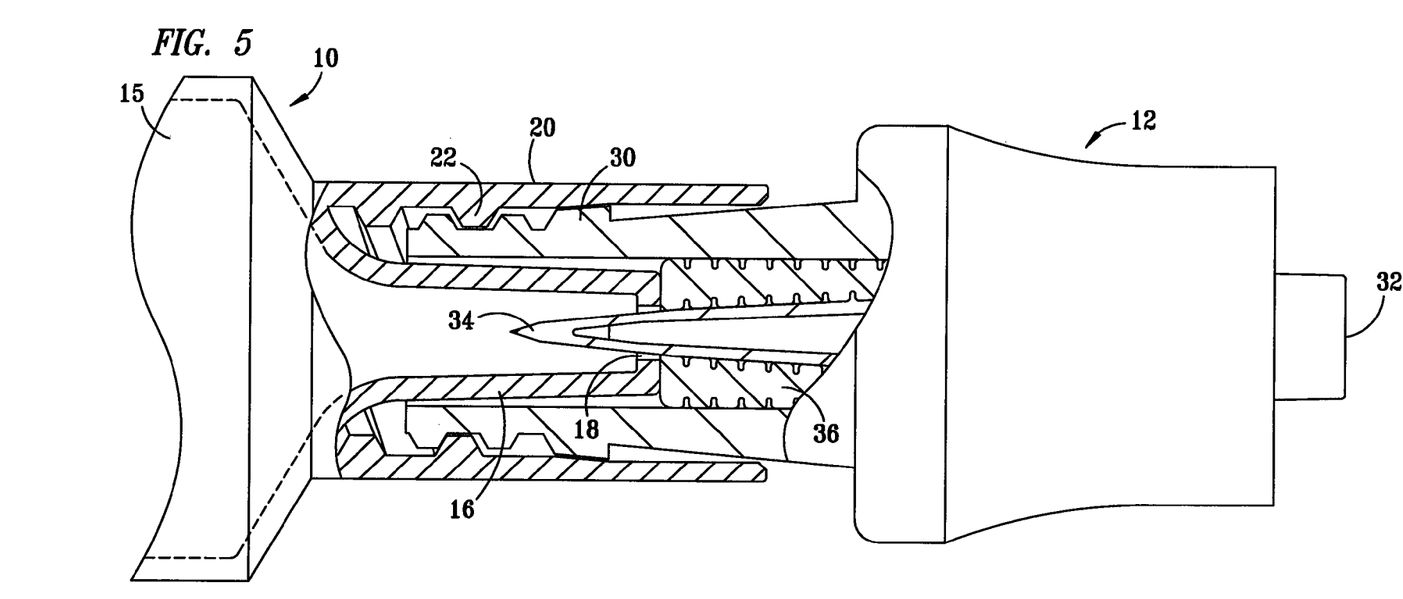
FIG. 5 is an enlarged detail view of the front portion of the syringe of FIG. 4, better illustrating the connection between the syringe and the CLAVE® connector.

Referring to FIG. 5, as CLAVE® connector 12 is being threaded into the front of pre-filled syringe 10, elastomeric support structure 36 moves relative to needle 34, thus exposing needle 34. When fully threaded together, elastomeric support structure 36 of CLAVE® connector 12 and nose 16 of pre-filled syringe 10 form a fluid-tight seal. When CLAVE® connector 12 is attached to pre-filled syringe 10, rearwardly facing needle 34 of CLAVE® connector 12 protrudes through nose opening 18. Medication flows from variable fluid chamber 15, through nose 16, through needle 34 and out CLAVE® connector 12 through forwardly facing open end 32, which is typically connected to a closed IV system. In a closed IV system, the forward end of a CLAVE® connector is attached to an IV tube, which is typically also in fluid communication with a bag or bottle containing a fluid being administered to a patient through another IV tube inserted into a patient's vein.

Although one preferred embodiment of the invention is described in relation to FIGS. 1-5, it will be understood by those of ordinary skill in the art upon reading this disclosure that forwardly projecting guard 20 of pre-filled syringe 10 can similarly be designed to accept frontal attachments other than a CLAVE® connector 12 provided that the projecting guard 20 extends beyond nose 16 so that nose 16 is recessed and protected from contamination, and provided that suitable cooperative attachment structures are provided as part of the syringe body and as part of the device to be attached to the syringe. It should be understood upon reading this disclosure that the frontal attachments can be connected at or near the front of a syringe body by the use of any suitable attachment method and structure having, for example and without limitation, threads, mounting lugs, twist locks, other abutting or frictionally engageable surfaces or interfaces, and other structures having cooperating elements adapted to secure the frontal attachment to a mounting structure on the front of the syringe body, which mounting structure is an integral part of or securely attached in fixed relation to the body of the syringe. The frontal attachments can be connected either releasably or permanently, but the attachment structure should not be susceptible to fluid leakage when subjected to such hydraulic pressures as are ordinarily experienced during use.

Figure 6:
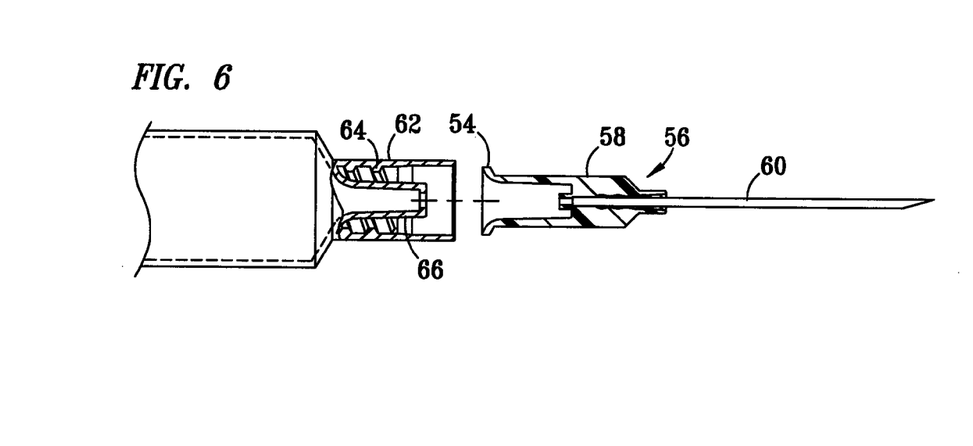
FIG. 6 is a side elevation view, partially in section, of the front portion of a syringe of the invention that is coaxially aligned with a needle assembly having a luer connector prior to attachment of the needle assembly to the syringe.
Figure 7:
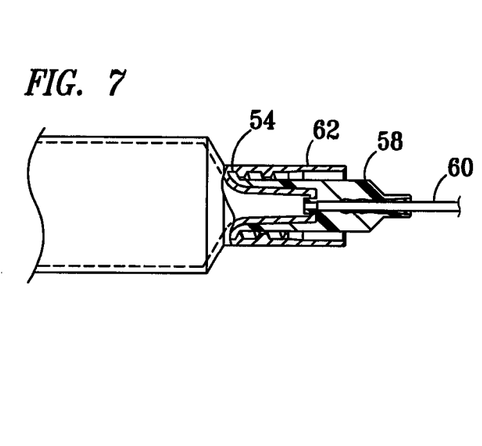
FIG. 7 is a side elevation view, partially in section, of the syringe and needle assembly of FIG. 6 after the needle assembly has been attached to the front portion of the syringe.

Referring to FIGS. 6 and 7, another preferred embodiment of the invention is shown wherein forwardly projecting, protective guard 62 extends forwardly past nose 66. Forwardly projecting guard 62, which is an integral part of or secured in fixed relation to the syringe body, has internal threads 64 that function as a mounting structure and are sized and configured to receive and cooperatively engage flange 54 of the luer connector of needle holder 58 of needle attachment 56. Needle assembly 56 further comprises needle 60 that is attached inside a smaller-diameter axial bore providing fluid communication through needle holder 58. Flange 54 of the luer connector of needle attachment 56 is desirably threaded into threads 64 of protective guard 62, creating a fluid-tight seal between nose 66 and luer lock needle attachment 56 that utilizes the full length of the cooperating, tapered engagement surfaces on the outside of nose 66 and the inside of needle holder 58. The luer connector embodiment as shown FIGS. 6 and 7 is intended only for illustrative purposes, and it should be understood and appreciated by those of ordinary skill in the art upon reading this disclosure that other similarly effective mounting structures that are an integral part of or permanently secured in fixed relation to the barrel can be used to attach a needle assembly to the front of a syringe, provided, however, that such structures embody elements that permit the use of a forwardly projecting, protective guard extending beyond the tip of the nose of the syringe and further provided that such protective guards can be used in a manner that is consistent with the stated purpose of preventing contamination by contact.

Figure 8:
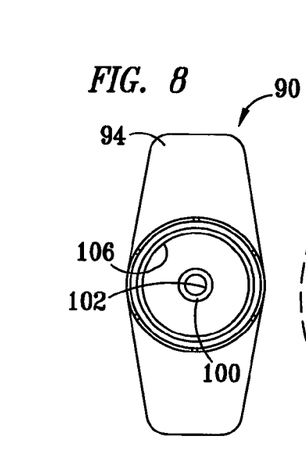
FIG. 8 is a front elevation view of a syringe having a guard made as part of the syringe body, the guard comprising an internally threaded cylindrical collar and a plurality of circumferentially spaced, longitudinally extending guard elements projecting forwardly from the cylindrical collar, with arcuate spacing between each most closely adjacent pair of guard elements that is substantially less than the width of each guard element.
Figure 9:
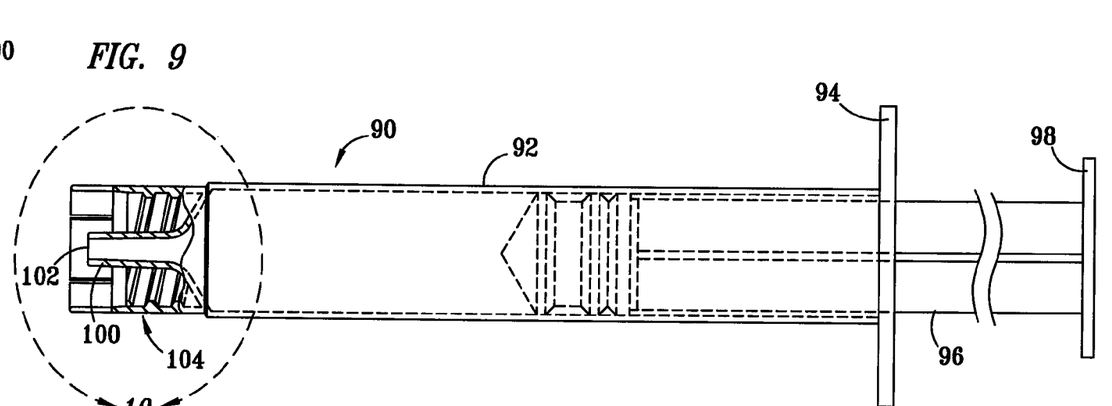
FIG. 9 is a side elevation view of the syringe of FIG. 8, with the front portion of the syringe shown in cross-section to illustrate how the guard projects forwardly of the nose of the syringe.
Figure 10:
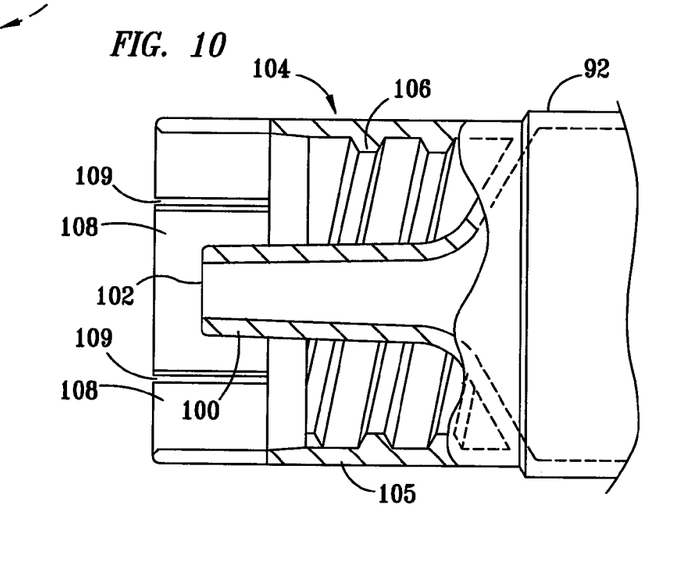
FIG. 10 is an enlarged detail view of the front portion of FIG. 9 that better illustrates the guard of FIGS. 8 and 9, and its relationship to the syringe body.

Referring to FIGS. 8-10, syringe 90 of the invention comprises tubular barrel 92 having a slidably engaged plunger 96 that can be manipulated using barrel flange 94 and end cap 98. Syringe 90 is desirably provided with a protective guard 104 (FIG. 10) that, as shown, is an integral part of the syringe body. Guard 104 comprises a cylindrical collar 105 with internal threads 106 and a plurality of circumferentially spaced, longitudinally extending guard elements 108 projecting forwardly from cylindrical collar 105, with a relatively narrow arcuate space 109 disposed between each adjacent pair of guard elements 108. In this embodiment, the width of spaces 109 is substantially less than the width of each guard element 108. Spaces 109 allow guard elements 108 to flex to greater extent than would be possible if guard 104 had a continuous cylindrical or outwardly tapered sidewall. The free ends of longitudinally projecting guard elements 108 of guard 104 extend forwardly beyond tip 102 of nose 100, and the width of elongate spaces 109 between them is preferably not great enough to permit the fingers of a clinician to pass between them and come into physical contact with nose 100. Because the open end of guard 104 that is opposite barrel 92 of syringe 90 extends longitudinally forward of the tip of nose 100, nose 100 is protected from physical contact that could contaminate it. Internal threads 106 are preferably sized to accept both CLAVE® connectors and needle attachments with luer connectors as previously described in relation to the syringes of FIGS. 3-7, and other similarly sized conventional frontal attachments not shown in the accompanying drawings.

Figure 11:
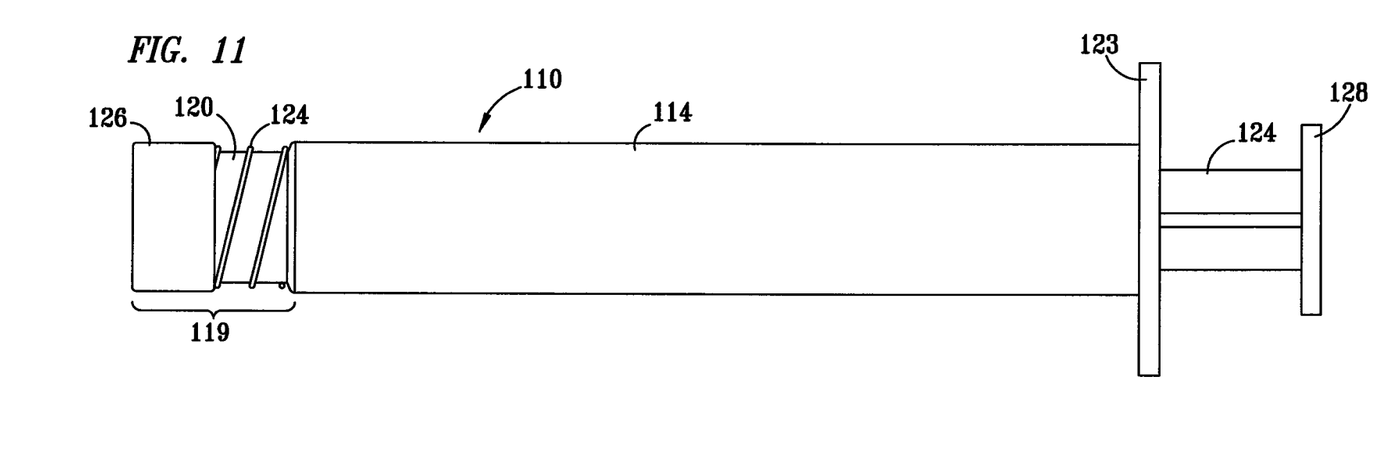
FIG. 11 is a side elevation view of another embodiment of the syringe of the invention showing a forwardly biased, projecting guard on the front end of the syringe.
Figure 12:
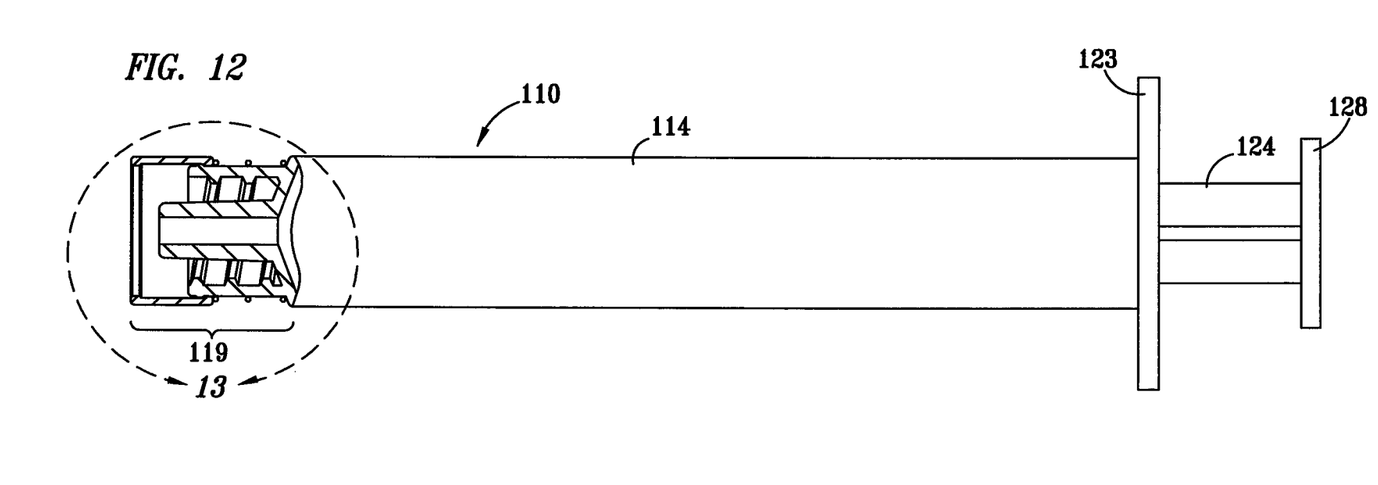
FIG. 12 is a syringe as shown in FIG. 11, but with the front portion shown in cross-section to illustrate how the guard projects forwardly of the nose of the syringe.
Figure 13:
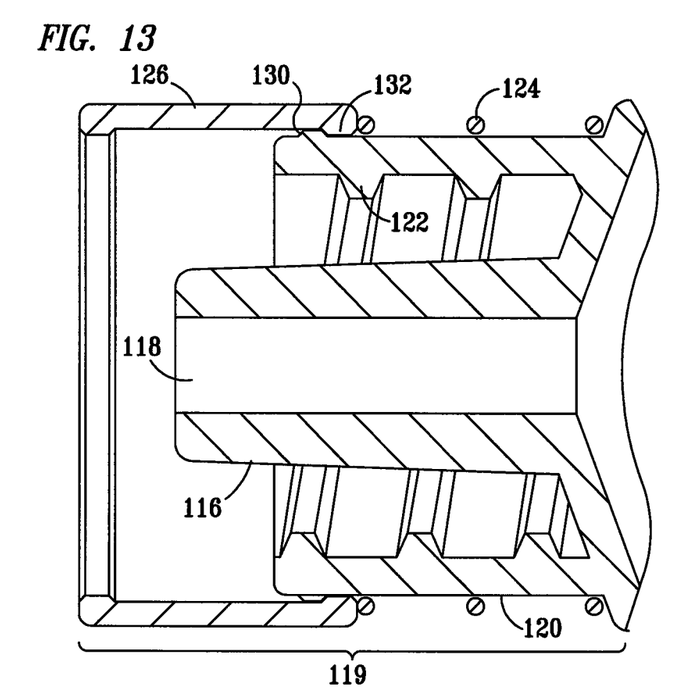
FIG. 13 is an enlarged detail view of the front portion of the syringe of FIG. 12 that better illustrates the forwardly biased guard projecting forwardly of the nose of the syringe.
Figure 14:
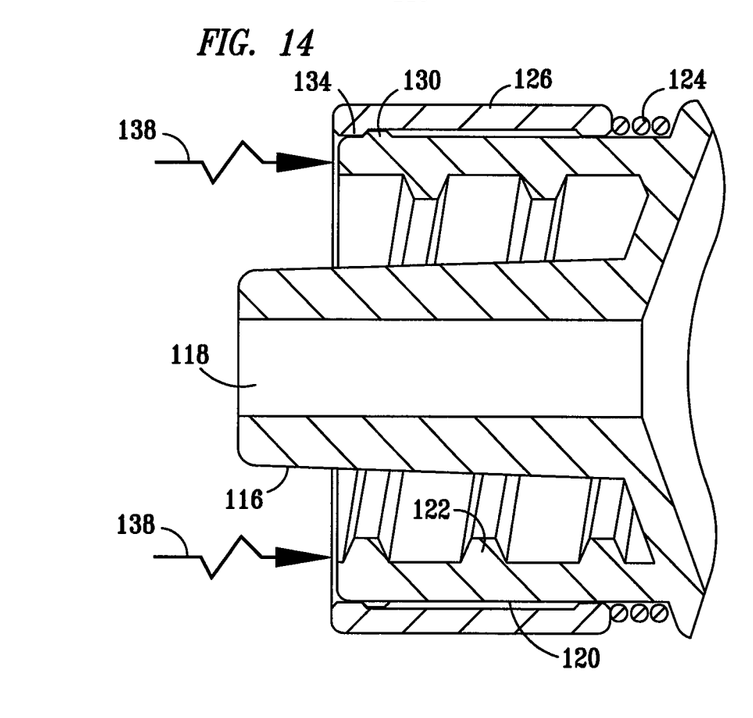
FIG. 14 is an enlarged detail view showing the front portion of the syringe of FIG. 13 wherein the guard is pushed rearwardly against the biasing force to uncover part of the nose of the syringe.

Referring to FIGS. 11-14, syringe 110 preferably comprises a body having a tubular barrel 114, finger grips 123, a front end portion or nose 116 having a longitudinal bore 118 with a front-facing opening; a plunger 124 with plunger handle 128 and a plunger seal (not visible) slidably engageable with the barrel; a unitarily molded mounting structure 120 with internal threads; and a protective guard 126 biased forwardly past the end of nose 116 by spring 124. The syringe body is preferably molded from a substantially transparent polymeric resin such as polypropylene, but other polymeric resins or glass are also acceptable materials. In this embodiment of the invention, the front end portion 119 of which is most easily seen in FIGS. 13-14, the forwardly extending end of nose 116 is recessed and protected from contamination by forwardly projecting, protective guard 126 that is attached to and supported by internally threaded mounting structure 120. A portion of nose 116 is encircled by mounting structure 120, and internal threads 122 are preferably sized and configured to accept conventional CLAVE® connectors, needle attachments with luer connectors (not shown), or other similarly sized frontal attachments. Protective guard 126 slidably engages the outside surface of mounting structure 120 and is moveable between an extended position (as shown in FIGS. 11-13) wherein spring 124 is expanded, and a retracted position (as shown in FIG. 14) wherein spring 124 is compressed by a force 138. When protective guard 126 is biased into its forwardly extending position, the front end of nose 116 is recessed and protected from contamination by physical contact.

Outwardly-facing annular boss 130 is preferably provided on mounting structure 120, and abuts against inwardly-facing annular boss 132 on protective guard 126, opposing the biasing force from spring 124 and preventing protective guard 126 from detaching from mounting structure 120 of syringe 110. Referring specifically to FIG. 14 wherein forwardly biased protective guard 126 is in its retracted position, spring 124 is compressed and nose 116 is no longer recessed. In this position, inwardly-facing annular boss 134 is abutted against outwardly-facing annular boss 130 on mounting structure 120, which prevents protective guard 126 from being retracted too far and over-compressing spring 124. The cooperation between annular bosses 130, 132 and 134 limits the range of motion of protective guard 126. Because of the expansion force of spring 124, protective guard 126 is always in its extended, protecting position until some additional rearwardly directed outside force 138 is exerted against it, either directly by the user or indirectly by an abutting surface of a frontal attachment as will occur, for example, during the attachment of a CLAVE® connector or other frontal attachment to the syringe.

Figure 15:
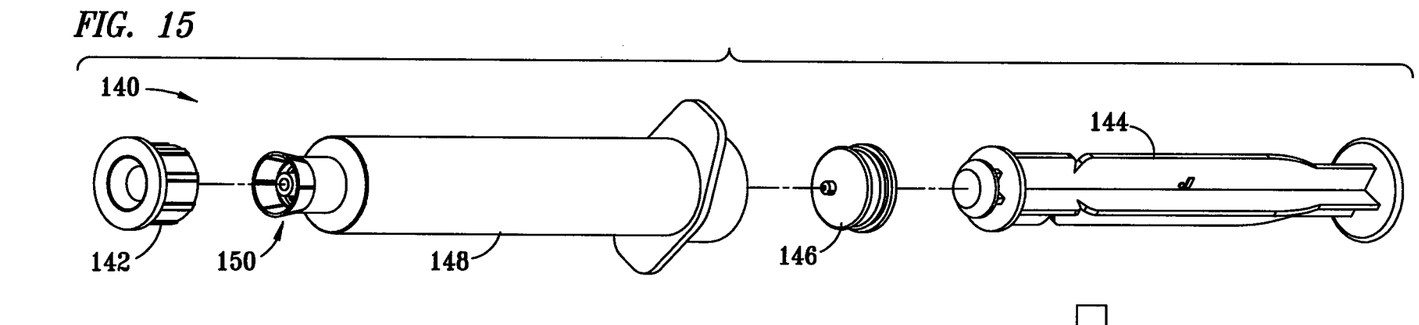
FIG. 15 is an exploded front perspective view of another embodiment of the invention having a protective guard that comprises a plurality of circumferentially spaced-apart guard elements, each of which has a free end that projects both forwardly and radially outward from the tip of the nose, which is shown in combination with a cooperating sealing cap that is installable on the front end of the syringe for shipping and storage, and is removable at the time of use.
Figure 16:
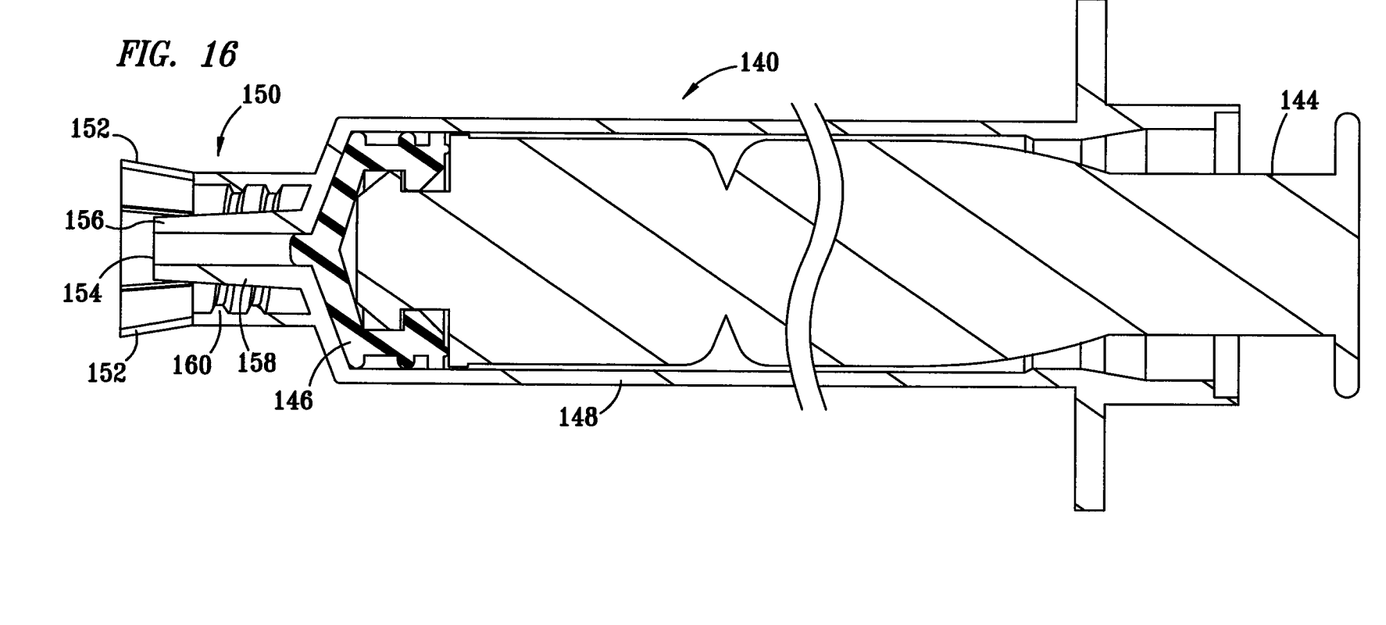
FIG. 16 is a cross-sectional side elevation view, partially broken away, of the syringe of FIG. 15, with the plunger inserted into the barrel and fully depressed to the position where it will rest at the conclusion of an injection.
Figure 17:
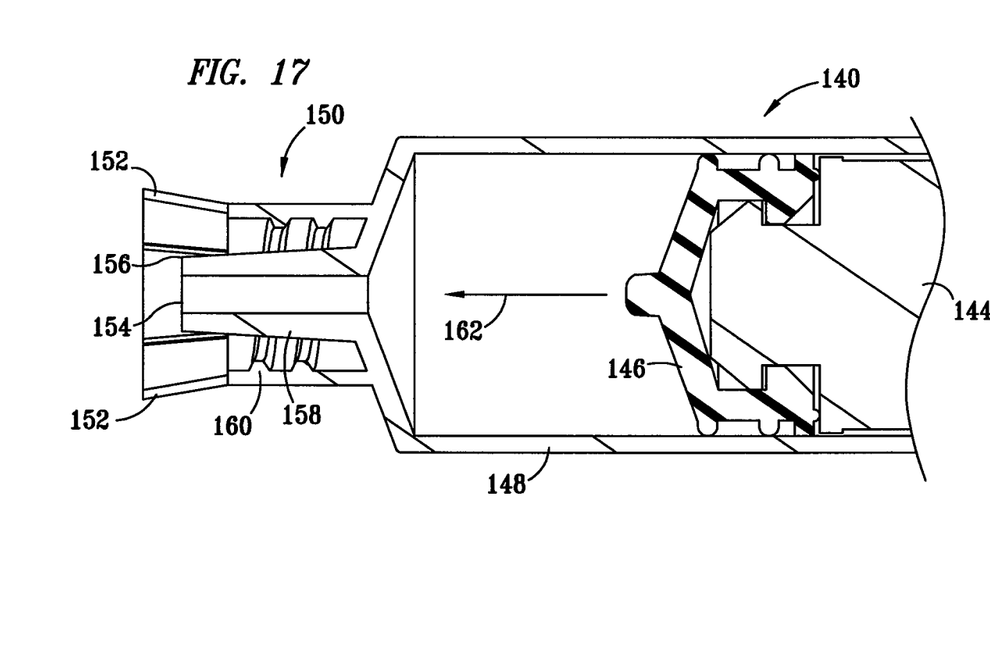
FIG. 17 is cross-sectional side elevation view of the front portion of the syringe of FIG. 15 wherein the plunger is inserted into the barrel and is moving forward relative to the barrel as it would be during an injection.

Still another preferred embodiment of the invention is described and explained in relation to FIGS. 15-18. FIG. 15 illustrates a syringe 140 that is similar in most respects to syringe 110 (as previously described in relation to FIGS. 8-10) in combination with a sealing cap 142 that is removed prior to use of syringe 140 with a frontal attachment. Syringe 140 comprises a barrel 148 with a slidably insertable plunger having a plunger handle 144 and a plunger seal 146, and a forwardly extending nose with a protective guard 150 that is further described in relation to FIGS. 16-17. Referring to FIGS. 16-17, protective guard 150, integral mounting structure 160 with internal threads, and nose 158 are unitarily molded as part of the body of syringe 140. Protective guard 150 further comprises a plurality of circumferentially spaced-apart, longitudinally extending guard elements 152 separated by elongate spaces 154. In this embodiment of the invention, in contrast to the embodiment of FIGS. 8-10, the forwardly facing free ends of guard elements 152 flare or taper radially outward relative to nose 158 as they extend away from mounting structure 160. FIG. 17 depicts plunger handle 144, with plunger seal 146 attached to its front end, moving forwardly through barrel 148 as indicated by arrow 162. FIG. 16 depicts plunger handle 144 and plunger 146 seated in the front end of barrel 148 following completion of an injection.

It will be understood and appreciated by those of ordinary skill in the art upon reading this disclosure that other materials such as, for example, paper, cardboard, foil, or a polymeric material can be used to fabricate a protective band that can similarly function as a protective guard for the nose of a medical device after the device is removed from its sterile packaging but prior to connection to a frontal attachment. Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

The invention claimed is:

1. A syringe having an internal fluid path, said syringe comprising:
   a body comprising a barrel, a protective guard, an integral mounting structure, and a nose; and
   a plunger inserted into sliding engagement with the barrel;
   wherein the nose comprises a luer connection surface and is insertable into fluid communication with a frontal attachment and is releasably connectable to the frontal attachment;
   the protective guard comprising a substantially cylindrical collar extending continuously around a longitudinally extending portion of the nose, and a plurality of circumferentially spaced-apart guard elements projecting forwardly in closely spaced relation from the substantially cylindrical collar;
   wherein the guard elements have forwardly facing free ends that flare radially outward relative to the nose and the substantially cylindrical collar as the free ends of the guard elements extend away from the mounting structure; and
   wherein the nose projects forwardly beyond the substantially cylindrical collar and the free ends of the guard elements project forwardly beyond the nose to recess the nose relative to the free ends of the guard elements and protect the nose from pathogenic contamination by contact.

2. The syringe of claim 1 wherein the syringe is pre-filled and further comprises a fluid-tight sealing cap.

3. The syringe of claim 1 wherein the nose has an axial bore disposed inwardly of the luer connection surface.

4. The syringe of claim 3 in combination with a sealing cap or a safety cap.

5. The syringe of claim 1 wherein an entirety of each of the spaced-apart guard elements is outwardly inclined relative to the substantially cylindrical collar.

6. The syringe of claim 1, wherein the mounting structure is disposed in fixed relation to the nose.

7. The syringe of claim 6 wherein at least part of the mounting structure is internally threaded.

8. The syringe of claim 1 wherein the mounting structure is unitarily made as part of the body.

9. The syringe of claim 1 wherein the mounting structure is configured to receive and secure the frontal attachment in fluid-tight engagement with the body.

10. The syringe of claim 9 wherein the nose projects forwardly beyond the mounting structure.

11. The syringe of claim 1 wherein the spaced-apart guard elements are separated by elongate spaces.

12. The syringe of claim 1 in combination with the frontal attachment.

13. The syringe of claim 12 wherein the frontal attachment is selected from the group consisting of a hypodermic needle assembly, a CLAVE® connector, a luer lock connector or other vascular access connector, and a luer-activated catheter hub.

14. The syringe of claim 13 wherein the frontal attachment is the hypodermic needle assembly further comprising at least one integrated needle safety component.

* * * * *